(12) United States Patent
Ramu et al.

(10) Patent No.: US 10,405,789 B2
(45) Date of Patent: Sep. 10, 2019

(54) IMPLANTABLE BLADDER FULLNESS SENSOR

(71) Applicants: Avner Ramu, Houston, TX (US); Nehemia Hampel, Bellaire, TX (US)

(72) Inventors: Avner Ramu, Houston, TX (US); Nehemia Hampel, Bellaire, TX (US)

( * ) Notice: Subject to any disclaimer, the term of this patent is extended or adjusted under 35 U.S.C. 154(b) by 214 days.

(21) Appl. No.: 15/643,567

(22) Filed: Jul. 7, 2017

(65) Prior Publication Data

US 2018/0008185 A1 Jan. 11, 2018

Related U.S. Application Data

(60) Provisional application No. 62/360,334, filed on Jul. 9, 2016.

(51) Int. Cl.
| | |
|---|---|
| *A61B 5/20* | (2006.01) |
| *A61B 5/00* | (2006.01) |
| *A61B 5/07* | (2006.01) |
| *A61N 1/36* | (2006.01) |

(52) U.S. Cl.
CPC .............. *A61B 5/204* (2013.01); *A61B 5/076* (2013.01); *A61B 5/746* (2013.01); *A61N 1/36007* (2013.01)

(58) Field of Classification Search
CPC ......... A61B 5/204; A61B 5/076; A61B 5/746; A61B 5/6874
See application file for complete search history.

(56) References Cited

U.S. PATENT DOCUMENTS

| | | | |
|---|---|---|---|
| 6,083,179 A | 7/2000 | Oredsson | |
| 7,610,093 B2 | 10/2009 | Gerber et al. | |
| 7,769,460 B2 | 8/2010 | Gerber | |
| 9,061,146 B2 | 6/2015 | Gerber | |
| 2006/0211951 A1* | 9/2006 | Milijasevic | A61B 5/204 600/547 |
| 2015/0141767 A1* | 5/2015 | Rogers | A61B 5/0084 600/301 |

FOREIGN PATENT DOCUMENTS

| | | |
|---|---|---|
| CN | 103598893 B | 2/2016 |
| WO | 2004037082 A1 | 5/2004 |

OTHER PUBLICATIONS

Provost, Benoit and Mohamed Sawan, Proposed new bladder volume monitoring device based on impedance measurement, Med. Biol. Eng. Comput., 1997, 35, 691-694.
Sawan, Mohamad, K. Arabi, Benoit Provost, Implantable volume monitor and miniaturized stimulator dedicated to bladder control, Artificial Organs, 1997, 21(3), 219-222.
Mendez, Arnaldo and Mohamad Sawan, Chronic monitoring of bladder volume: a critical review and assessment of measurement methods, Canadian Journal of Urology, Feb. 2011, 18(1), 5504-5516.

* cited by examiner

*Primary Examiner* — Paula J Stice
(74) *Attorney, Agent, or Firm* — Richard A Baker, Jr.

(57) ABSTRACT

An apparatus for determining the volume of urine in a human bladder is described. The apparatus uses light to determine the length of a flexible tube attached vertically to the outside of the bladder, and converts the length into a fullness value that is transmitted to an external device that notifies a user about the state of the bladder.

14 Claims, 4 Drawing Sheets

IMPLANTABLE BLADDER FULLNESS SENSOR

RELATED APPLICATIONS

This application claims the benefit of U.S. provisional patent application 62/360,334, "Implantable Bladder Fullness Sensor", filed by Avner Ramu and Nehemia Hampel on Jul. 9, 2017. This provisional patent application is incorporated herein by reference.

BACKGROUND

Technical Field

The devices described herein are directed to implantable medical devices, and more specifically to implantable sensors for determining the changes in the urinary bladder volume, with or without nerve stimulation.

Description of the Related Art

Urinary incontinence, or involuntary urination, is a common condition afflicting in particular, people with spinal cord injuries or diseases, people with neurocognitive disorders, women of all ages, and elderly men. Urinary incontinence results from several types of malfunctions of the lower urinary tract. In adults the normal role of the lower urinary tracts is to collect, store, and release the urine at will. While in elderly men prostate enlargement is an important cause for urinary frequency and incontinence, in the majority of patients who do not suffer from this condition it is caused by a variety of neuro-muscular dysfunctions.

Normally, as the urinary bladder, which receives the urine that is produced by the kidneys, fills up, stretch receptors in its wall send trains of signals via nerve fibers to the lower part of the spinal cord. The frequency of these signals increases as the volume of the urinary bladder enlarges. Some of this information reaches local neural centers in the lower spinal cord, and some of it ascends via the spinal cord to the brain, which translate it to conscious awareness about the degree of the urinary bladder fullness. This information allows a person to determine when to urinate. If in spite of awareness that his urinary bladder has been enlarged, a person decides to temporarily avoid from urinating, his brain will send down the spinal cord blocking messages to the neuronal centers of the lower spinal cord, to prevent them from independent activity. In addition it will also activate the contraction of the external urethral sphincter. When the neural centers of the lower spinal cord are independent of brain control, as they receive a critical frequency of signals from the bladder's stretch receptors they instruct (via nerves that exit the spinal cord and reach the lower urinary tract), the muscle of the urinary bladder wall to contract and at the same time they order the muscle at the outlet region of the urinary bladder to relax. This activity results in urination. As this independent activity of the lower spinal cord and urinary tract is not supervised by consciousness it is considered as autonomic reflex urination.

As described above conscientious activity could prevent the autonomic reflex urination. On the other hand, when the conscientious brain decides that the person should urinate, it stops from blocking the activity of the neural centers in the lower spinal cord, and at the same time it also send a neuronal message that orders the external urethral sphincter to relax. As a result of this activity urination occurs.

Any disturbance in the neuronal circuits that normally allows the conscientious brain to control the urination process will result in urinary incontinence. There are several types of urinary incontinence such as "Urge", "Stress", and "Overflow." but in all of them the patient may not become timely (or at all) aware that the autonomic reflex urination is about to occur.

Therapies for treating urinary incontinence include: medications, absorbent products, collecting systems, occluding devices, indwelling or intermittent catheters, a variety of behavioral exercises, various types of surgeries, Posterior tibial, Sacral or Pudendal electrical nerve stimulation devices. All these therapies had achieved some success, and some of them involve significant risk of complications. It seems likely that the results achieved by the procedures of nerves stimulations that are currently employed independently of the degree of bladder fullness could be much improved if the nerve stimulation would be delivered at times dependent on the degree of bladder fullness. Knowledge about the degree of bladder fullness also can help the patient or a care giver to determine when to apply maneuvers or other procedures that initiate urination under more convenient and less embarrassing conditions.

A number of approaches have been undertaken to resolve the issue of sensing the urinary bladder volume. For instance, Metronic, in U.S. Pat. No. 9,061,146 (incorporated herein by reference), describes the use of impedance in an electrical circuit to determine the amount of liquid in the bladder (known as Electrical impedance plethysmography). Medtronic uses probes implanted on both sides of the bladder and then uses changes in impedance to estimate the fullness of the bladder. However, as reported by Arnaldo Mendez and Mohamad Sawan in "Chronic monitoring of bladder volume: a critical review and assessment of measurement methods" (incorporated herein by reference), this method has shown problems with reliability, repeatability, and accuracy.

Another solution, is an intravesical pressure transducer for measuring the pressure inside the bladder cavity. However bladder cavital pressure does not correlate well with the degree of the stretch receptor activation which triggers the autonomic reflex urination. Any intravesical device is prone to damage the bladder mucosa and cause infections, inflammations, and the formation of bladder stones.

Strain-gauge plethysmography uses transducers that change their electrical charge based on the modification of shape caused by external forces. These transducers use resistive, capacitive, inductive or piezoelectric techniques. See J Upfal in PCT application WO2004037082 (incorporated herein by reference). These proposed solutions have not been tested, and require significant technological engineering to make the materials soft and elastic, have high endurance, and biocompatibility, with the ability to fit the irregular shape of the bladder.

Another solution uses Wearable Ultrasonography to continuously take an ultrasound of the bladder. Ultrasound is considered to be the most accurate method. However, the device is not portable with today's technologies.

Still another option is Electromagnetic plethysmography which attaches a permanent magnet to the bladder wall and also attaches Hall Effect transducers to the bladder wall. The Hall Effect transducers then sense the distance to the magnet. This has only been tried in animal studies, and the in vivo accuracy is not known. However, the robustness of this solution relies on the positioning of the magnet and the Hall Effect sensors.

The present invention, eliminates the issues articulated above as well as other issues with the currently known products.

SUMMARY OF THE INVENTION

An implantable device for determining a volume of a urinary bladder is described. The device is made up of a flexible, surgical grade tube, attached to an outer surface of a urinary bladder, where the length of the tube expands as the volume of the urinary bladder increases. Inside of the tube is a light source at one end of the tube and a photocell either at the other end or at the same end of the tube, if there is a reflective material, such as a mirror, at the opposite end. Electronic circuitry is electrically connected to the light source and the photocell where the electronic circuitry periodically causes the light source to transmit one or more light waves into the tube and then counts a period of time until the photocell detects the arrival of the light waves. The electronic circuitry calculates the volume of the urinary bladder based on the length of the tube, as determined based on the period of time for the light wave to travel between the light source and the photocell.

In some embodiments, the implantable device also includes a communication module connected to the electronic circuitry for transmitting information related to the volume of the urinary bladder to an external instrument. The external instrument could be a smart phone, a cell phone, a watch-like device (iWatch, FitBit, etc), a computer or other electronic device. The external instrument could produce an audio, visual, or physical (small electronic shock, pinch, vibration) alert when the bladder reaches a pre-determined level.

A method for determining the volume of a urinary bladder is also described. The method comprises the steps of generating one or more light waves from a lighting source located inside of a flexible, surgical grade tube, at one end of said tube, where the tube is attached to an outer surface of a urinary bladder. The lighting source is electrically connected to electronic circuitry. The electronic circuitry counts a period of time the light waves take to be received by a photocell, where the photocell electrically connected to the electronic circuitry. The electronic circuitry calculates the distance that the light wave traveled from the lighting source to the photocell using the period of time, and the distance is compared to a baseline distance representing a length of the urinary bladder at a known volume to determine the volume of the urinary bladder.

The method could also include alerting a user when the volume of the urinary bladder reaches a predetermined level or monitoring the volume of the urinary bladder to calculate a rate of increase in the volume of the urinary bladder. The method could also include reflecting the one of more light waves with reflective material positioned at one end of the tube. The method could also include the transmission of the period of time, the distance or the volume to an external instrument, such as a smart phone, a cell phone, a watch-like device (iWatch, FitBit, etc), a computer or other electronic device. The transmission could be via Bluetooth, WiFi or similar protocols.

A system for determining a volume of a urinary bladder a urinary bladder sensor and an external instrument. The sensor is made up of a flexible, surgical grade tube, attached to an outer surface of a urinary bladder, where the length expands as the volume of the urinary bladder increases. Inside of the tube is a light source at one end of the tube and a photocell either at the other end or at the same end of the tube, if there is a reflective material, such as a mirror, at the opposite end of the tube. Electronic circuitry is electrically connected to the light source and the photocell where the electronic circuitry periodically causes the light source to transmit one or more light waves into the tube and then counts a period of time until the photocell detects the arrival of the light waves. A communication module connected to the electronic circuitry for transmitting information related to the volume of the urinary bladder to an external instrument. The external instrument is made up of a network module for receiving the information transmitted from the sensor's communications module and an application for processing the information. The external instrument also has an interface to a user for notification the user of the state of the urinary bladder.

The external instrument's interface to a user could include an audio alert or a visual alert on a display screen. The external instrument could be a smart phone, a cell phone, a watch-like device (iWatch, FitBit, etc), a computer or other electronic device. The communications module and the network module could use a Bluetooth protocol to transmit the information. The calculation of the volume of the urinary bladder is based on the length of the tube, as determined based on the period of time for the light wave to travel between the light source and the photocell. The calculation could be done in the electronic circuitry in the sensor or in the external device, or in both.

DETAILED DESCRIPTION OF THE INVENTION

Figure 1:
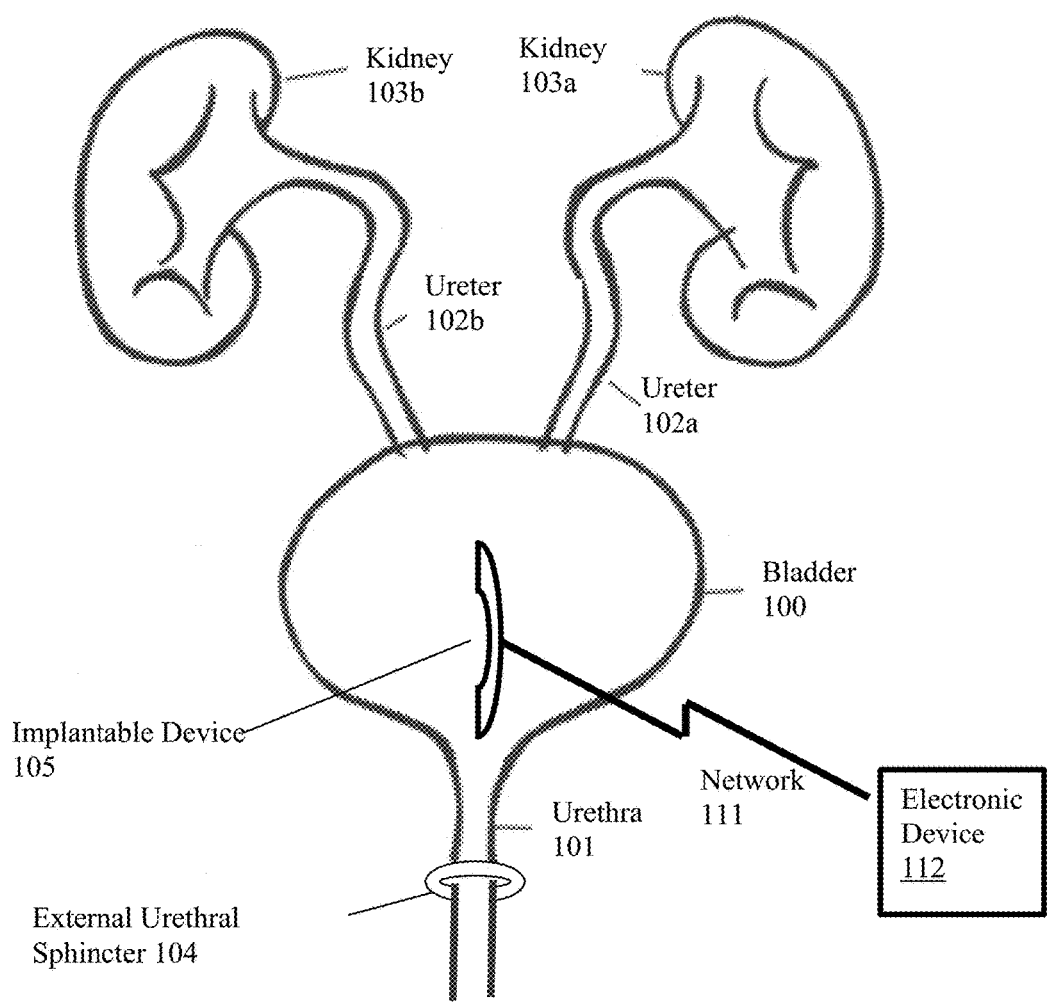
FIG. 1 is a diagram of the human urinary system with the volume sensor attached.

Normal micturition (urination) is a process of periodic discharge of urine from a reservoir (urinary bladder 100) through the urethra 101. See FIG. 1 for a diagram of the anatomy. In infants and young children it occurs involuntarily, and at older ages it is regulated at will. This acquired "skill" is the result of learned behavior.

Micturition is a coordinated activity of the bladder 100 and the urethra 101 which are controlled by a complex neural circuitry that involves the brain, the spinal cord, the somatic (voluntary) nervous systems, and the peripheral nerves and ganglia of the autonomic neural systems. Owing to the complexity of the neural mechanisms that regulate micturition, the process is particularly sensitive to various injuries, diseases and degenerative changes.

Involuntary urination (urinary incontinence=UI) is a common health problem that affects the quality of life of those who lost the voluntary ability to urinate. It is estimated that one third of all the people over the age of 60 have some degree of UI. It is also known that the incidence of UI increases with age. There are several other groups of patients with UI, where the condition is not age-related (e.g. patients with spinal cord injuries).

There are several types of UI that should be treated according to the pathological mechanisms involved. Unfortunately, the current treatment modalities (medication, intermittent occluding devices and catheters, surgical procedures, and nerve stimulation) are often far from being satisfactory. The following description is the basis for our proposed remedies to several types of UI.

Involuntary urination occurs when the activity of the somatic level of control of micturition is disrupted, and the function of the lower urinary tract (bladder 100 and urethra 101) becomes strictly regulated by the autonomic nervous system (both sympathetic and parasympathetic).

In general, when the sympathetic nerves are activated, they relax the smooth muscle of the bladder's wall (detrusor), and at the same time they cause the smooth muscle in the bladder neck and around the urethra 101 to contract. As long as this activity continues, the bladder 100, that receives, through the ureters 102a, 102b, the urine produced by the kidneys 103a, 103b, will gradually increase in volume. In normal adults the bladder 100 can accumulate several deciliters of urine.

The parasympathetic nervous system action in the lower urinary tract works in opposition to that of the sympathetic system. Activation of the parasympathetic system results in the contraction of the detrusor and the relaxation of the smooth muscle around the urethra 101. The result of the parasympathetic activity is the expulsion of urine from the bladder 100 through the urethra 101.

Obviously, the activities of the sympathetic and parasympathetic nervous systems of the lower urinary tract do not occur simultaneously. Neuronal centers in the lower spinal cord determine when one or the other system is activated. These neurons receive signals from sensors in the wall of the bladder 100 that are activated by stretching of the bladder 100. When the neurons in the lower spinal cord receive a certain frequency of pulses from these sensors, they activate the parasympathetic nerves and at the same time inhibit the activity of the sympathetic nerves, and therefore trigger urination. This process is referred to as "reflex micturition."

When the somatic (voluntary) neuronal system of the lower urinary tract is intact, one of its effects is to regulate the degree of contractility of the external urethral sphincter 104. Other components of this system can suppress or activate the spinal neuronal centers that regulate the activity of the sympathetic and parasympathetic influence on the smooth muscles of the bladder 100 and of the urethra 101.

As mentioned above, the bladder's stretch-sensors convey information about the bladder 100 fullness, to the spinal cord (through the nerves that innervate the bladder 100). In addition to reporting to the spinal neuronal centers that regulate the micturition reflex, this information is also transferred through spinal tracts that reach several brain centers that are involved in the somatic control of the lower urinary tract. The information transmitted to the brain allows the individual to be aware of the degree of bladder 100 fullness and to initiate a voluntary micturition (through activation of the efferent arm of the somatic system).

This description of the neuronal control of micturition indicates that some of the involuntary urination conditions could be remedied by substituting the damaged afferent arm of the somatic neuronal circuit, which is involved in regulating the activity of the lower urinary tract, with artificial systems.

These systems will make the patient aware of the degree of bladder 100 fullness so that he/she will be able to activate at will the efferent arm of the somatic system and initiate micturition.

This artificial system could also benefit patients where both arms of the somatic system are non-functional, by indicating to the patient when to use certain maneuvers that trigger reflex micturition. In other patients in which reflex micturition cannot be triggered by manipulation, the artificial system will notify the patient (or a care-giver) as to when to expect an involuntary micturition and thus give them the time and opportunity to void in the toilet or into a urine collecting device.

The most desirable form of such an artificial system is in the form of an implantable small device 105. There are several optional parameters that may be used for constructing an artificial system to fulfill the required functions.

In the future, by combining such an instrument with electrical stimulation of the pudendal, and/or pelvic and/or hypogastric nerves for relaxing or contracting the detrusor, other types of urinary incontinence may also be ameliorated.

Volume Sensor

The most desirable form of such an artificial system is in the form of an implantable small device 105 (about the size of clinically implantable pacemakers) that will report to an external instrument 112. The implantable urinary bladder volume sensor 105 part of the device will be vertically attached to the outer surface of the bladder 100. In the preferred embodiment, the bladder volume sensor 105 is attached vertically to the anterior side of the urinary bladder 100.

The implantable device 105 will be connected electrically to a system that will sense the changes in the volume of the bladder 100. It will contain a remotely chargeable battery 304, and a wireless system 303 that will transmit the detected signals to an external instrument (a watch-like, and/or to a smart phone) 112.

The typical human adult bladder 100, when full can contain 500-750 ml of urine. When empty it length (vertical) is about 5 cm and when maximally full: 15 cm long. However, the normal urge to urinate is when the bladder 100 is about ¼ full.

Figure 2:
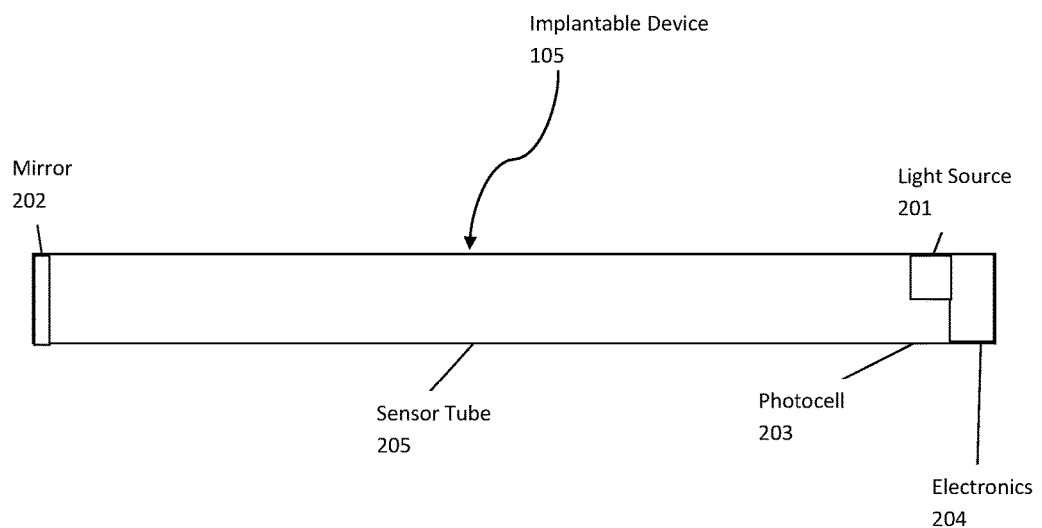
FIG. 2 is a drawing of the volume sensor device showing a possible physical location of the device.

As seen in FIG. 2, the volume sensor part of the implantable device 105 will be made of 5 cm long biologically inert tube (Silastic, Dow Corning) with a light source 201 and a photocell 203 (separated from each other) at its bottom end and a mirror 202 at its upper end. The energy for the light source 201 and the photocell 203 will come from the battery 304 (see FIG. 3). The measurement of the time between the activation of the light source 201 and the light activation of the photocell 203 (defined as the light transit time) could be measured once every 20 minutes. The light transit times between light source 201 activation and photocell 203 detection will be used to determine the change in vertical length of the bladder. The photocell 203 could be any device capable of the detection of light or similar waves, such as optical sensors, solar cells, photo detectors, photoelectric sensors, or similar devices. The light source 201 could be any device capable of generating light or similar waves, such as LEDs, lasers (semiconductor or other), incandescent light, or similar devices. In another embodiment, the photocell 203 and the light source 201 could be replaced by devices that communicate using other forms of waves, such as radio waves, IR waves, UV waves, ultrasound, or acoustic waves.

The information about the measurements of the light transit times will be transmitted by a wireless system 303 (in FIG. 3) to an external instrument 112 that will process this information and turn it to information that the patient (or caregiver) can comprehend. The computational ability of the external instrument 112 will allow periodic recalibration.

The calibration of the device will be carried out in vivo by standard urometrics.

Looking to FIG. 1, the anatomy of the urinary system is shown. The kidneys 103a and 103b are each connected to a ureter 102a and 102b. The ureters 102a and 102b allow urine to flow from the kidneys 103a and 103b to the bladder 100. The bladder 100 stores the urine until it is voided through the urethra 101.

The urinary bladder would be exposed through an anterior standard surgical approach, and the implantable device 105 will attached to the base of the exposed bladder using sutures. The positioning of the implantable device will be such that its volume sensor part would be placed vertically to the bladder and its position secured by sutures. The vertical length of the bladder increases as it fills up with urine. This will enlarge the length of the sensor tube 205 (see FIGS. 1 and 2) that is attached vertically to the outer side of the urinary bladder.

FIG. 2 shows one possible embodiment of the structure of the volume sensor part of the implantable device 105. The sensor tube 205, in some embodiment, is about a 5 cm surgical grade flexible tube such as Dow Corning's Silastic® tubing. A mirror 202 is attached to the upper end of this tube 205. At the lower end of the tube, there is a light source 201, and a photocell 203, both are separated by a light impermeable barrier and both connected to the electronic circuits 204 that supply electric energy to the light source 201, and receive the current change induced by light reaching the photocell. In other embodiments the locations of these components could be rearranged.

The electronics 204 are electronically connected to the light source 201, and determines when the light source 201 is activated. The time that the light source 201 is activated is precisely determined relative to the time that the light is detected by the photocell 203. The light source 201 sends the light down the sensor tube 205 to the mirror 202 at the other end of the sensor tube 205. The light reflects off of the mirror 202 and returns to the photocell 203. When the light hits the photocell 203, the electronics 204 records the time difference between the time the light is generated by the light source 201 and when the light is received by the photocell 203. This time is then multiplied by the speed of light (29,979,245,800 cm/s) and the product gives the length that the light passes between the light source, the mirror and the photocell. For a tube length of 5 cm, round trip time is 0.003333 μsec. elongation of the tube by 1 cm will increase the light travel time by 0.000666 μsec. Given this range of time changes, the electronics 204 will use custom made circuitry for measuring the time differences. In another embodiment, a high speed processor 301 (see FIG. 3) would clock the light transition times.

Figure 3:
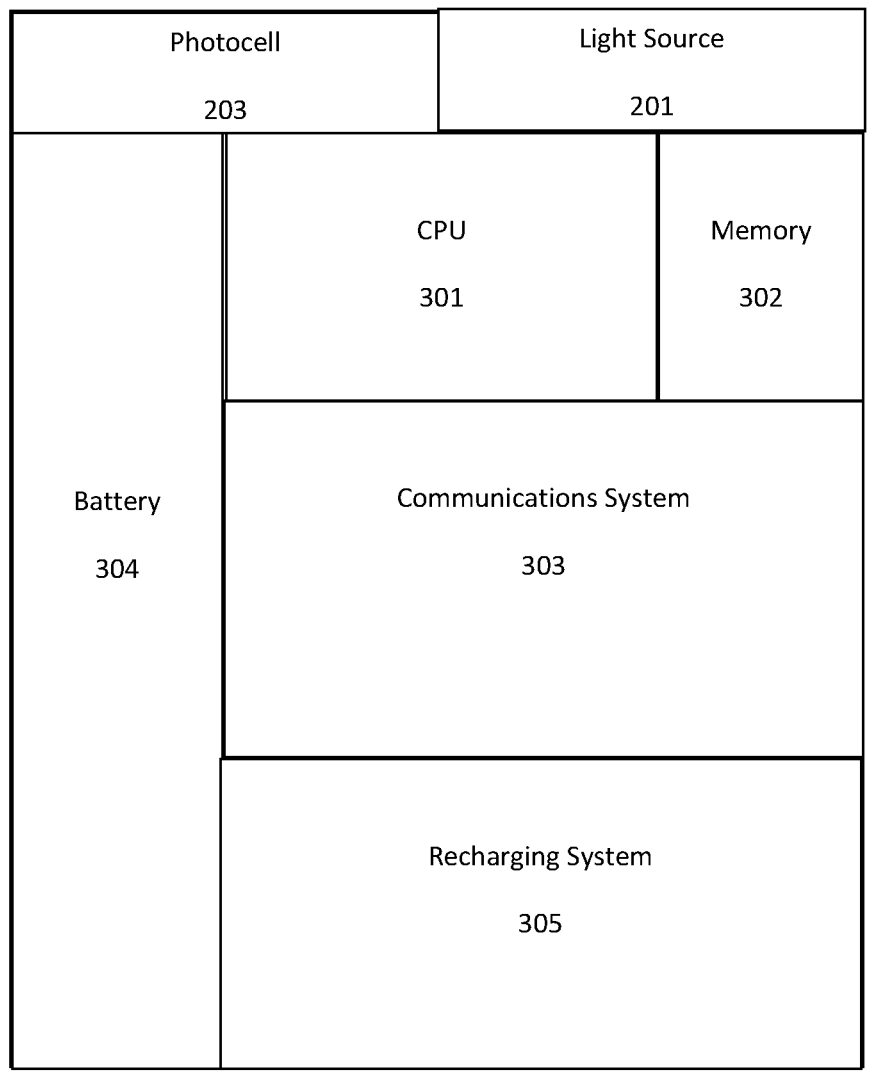
FIG. 3 is an electrical block diagram of the volume sensor device.

FIG. 3 shows a block diagram of the electronics. Battery 304 powers the photocell 203, light source 201, CPU 301, memory 302, and communications system 303. In one embodiment, a wireless charging system 305 (such as Tech-Novator's XE product or products from Energous or Ossia), is used to convert radio waves into power to recharge the battery 304. Another embodiment recharges using body heat or energy captured from the body. In other embodiments, the battery 304 is replaced surgically every time the battery needs recharging, perhaps every 10-15 years if a high quality long lasting battery, such as those used for pacemakers, is used. In still another embodiment, small wires are brought through the patient's skin for directly recharging.

The communications system 303 is used to communicate with the patient using Bluetooth, Wi-Fi, cellular, or other wireless frequencies and protocols 111. The communications system 303 is connected to the CPU 301, and may be integrated with the CPU 301. For instance, the CPU 301 and communications system 303 could be a Cypress PSOC system on a chip. In one embodiment, the communications system 303 connects with an Apple iWatch (or similar device) 112. The status of the fullness of the bladder 100 is communicated from the CPU 301 through the communications system 303 wirelessly over a Bluetooth Low Energy (BLE) protocol 111 to the iWatch 112.

The iWatch (or similar device) 112 may have an app running that displays the fullness of the bladder 100. It may also sound an alarm to alert the user when the user needs to head to the bathroom because the bladder is filling up. The iWatch 112 could be replaced by a computer 112, a stand-along device or could alert a nurse or a nursing station. In another embodiment, the wireless signal 111 could be sent to a device implanted elsewhere in the patient. This device could signal the patient's nervous system or the patient's brain that the patient's bladder is reaching a certain level of fullness.

The CPU 301 is electrically connected to and instructs the light source 201 to turn on the light. The CPU 301 is also electrically connect and receives signals from the photocell 203. In some embodiments, a high speed counter, such as the On Semiconductor MC10E137 8 bit ripple counter, is connected to the interface between the CPU 301 and the light source 201, starting the counting when the CPU 301 instructs the light source 201 to turn on. The counter counts the number of nanoseconds until the photocell 203 detects the light reflected off of the mirror 202. The CPU 301 then reads the count of nanoseconds from the counter. The MC10E127 can count in less than 0.5 nsec increments. For instance, if a 2 GHz crystal is used for clocking the MC10E127, each will be 0.5 nsec.

CPU 301 has memory 302 either integrated or electrically connected for storing data during processing. The CPU 301 is either integrated with or electrically connected to the communications system 303 for transmitting information to other devices.

CPU 301 may receive its power from the battery 304 or through other power source. In one embodiment, radio signals could power the entire device directly, powering a capacitor that starts the CPU 301, turns on the light, counts the nsec before the light returns, and returns the count through the communications system on the power received from the radio signal, similar to an RFID system.

Figure 4:
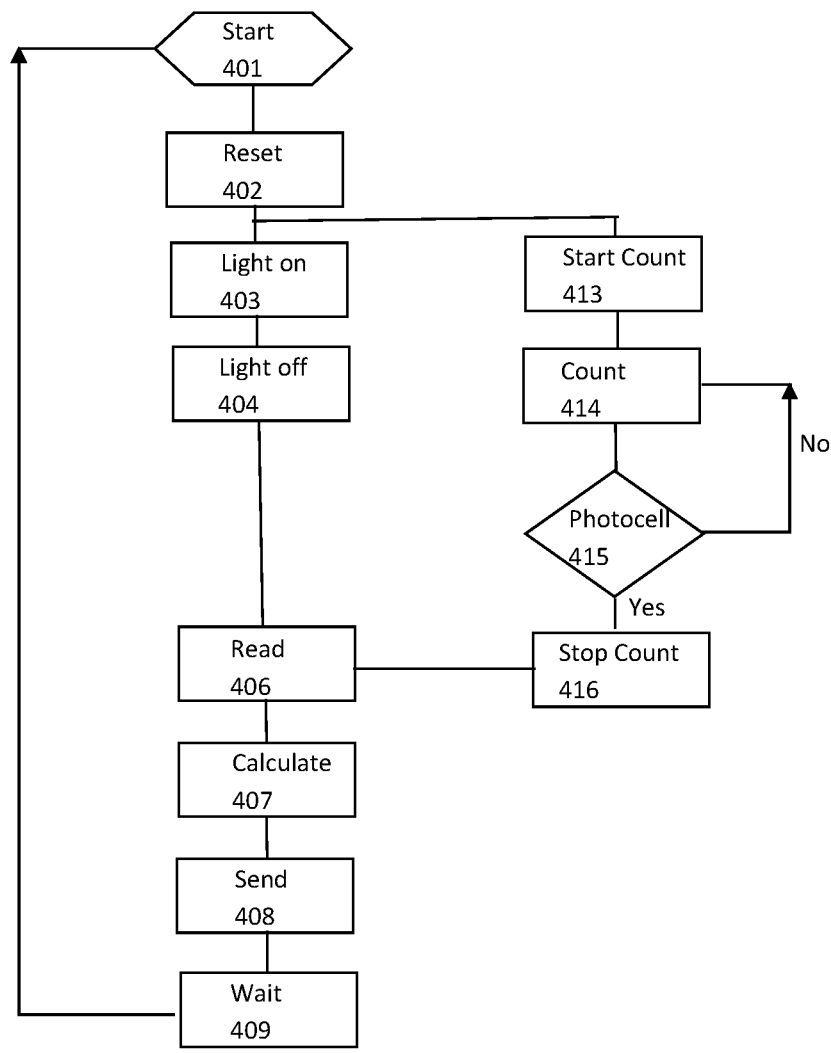
FIG. 4 is a flow chart of a software implementation of the volume sensor device.

FIG. 4 shows a flow chart of one embodiment of an algorithm that could be used. The process starts 401 by initializing the CPU 301. Next, the counter is reset 402 to zero. Then, simultaneously the light 201 is turned on 403 and the counter is started 413. The light 201 is turned off 404 after a short time, perhaps a few nsec. Asynchronously, the counter increments counts the time 414. In one embodiment, a very high speed counter is used, and a 2 Ghz clock is connected to the counter. Thus, each increment of the counter is 0.5 nsec of time. The counter continues counting until light is detected 415 by the photocell 203. Once the light is detected, the counter will stop 416. In another embodiment, the counting could be done by the CPU 301 itself.

In one embodiment, the CPU 301 detects that the photocell 203 has detected the light, and it reads the count from the counter 406. In one embodiment, the CPU converts the count into a percent of fullness of the bladder by calculating 407 the count times a constant pre-calculated that relates to the speed of light, distance, and how full the individual patient's bladder is at a specific distance. Calculation 407 does not have to be done in the CPU 301, and could be done in another device, the iWatch for example. The fullness indication from the calculation or the raw count is then sent 408 via the communications system 303 to another device, the iWatch for example.

In one embodiment, the constant used in the calculation 407 is determined by observing the bladder using an external ultrasound device to view the actual fullness of the bladder while executing the algorithm to read the raw count from the counter, and recoding the count at various stages of fullness (for calibrating the implantable device, the actual fullness of the bladder could also be determined using other commonly used urometric devices). This is then used as the constant in the calculation. Or, if the fullness calculation is found not to be linear, using a best fit curve or as a lookup table.

The algorithm then could wait for 20 minutes 409 and then repeat the process starting at the reset 402. In another embodiment, the process could stop once the data is sent in step 408.

The foregoing devices and operations, including their implementation, will be familiar to, and understood by, those having ordinary skill in the art.

The above description of the embodiments, alternative embodiments, and specific examples, are given by way of illustration and should not be viewed as limiting. Further, many changes and modifications within the scope of the present embodiments may be made without departing from the spirit thereof, and the present invention includes such changes and modifications.

The invention claimed is:

1. An implantable device for determining a volume of a urinary bladder comprising:
    a flexible tube, attached to a surface of a urinary bladder, with a length that expands as the volume of the urinary bladder increases;
    a light source inside of the flexible tube at an end of said flexible tube;
    a photocell inside of the flexible tube at an end of said flexible tube, positioned such that one or more light waves from the light source are received by the photocell; and
    electronic circuitry electrically connected to the light source and the photocell where the electronic circuitry is configured to periodically cause the light source to transmit the one or more light waves into the flexible tube and then counts a period of time until the photocell detects an arrival of the light waves, said electronic circuitry is configured to calculate the volume of the urinary bladder based on the length of the flexible tube, as determined based on the period of time for the light waves to travel between the light source and the photocell.

2. The implantable device of claim 1 further comprising reflective material inside of the flexible tube at an end opposite from the light source.

3. The implantable device of claim 1 further comprising a communication module connected to the electronic circuitry for transmitting information related to the volume of the urinary bladder to an external instrument.

4. The implantable device of claim 3 wherein the external instrument is a smart phone.

5. The implantable device of claim 3 wherein the external instrument is a watch-like device.

6. The implantable device of claim 3 wherein the external instrument is a computer.

7. The implantable device of claim 3 wherein the external instrument produces an audio alert when the volume of the urinary bladder reaches a pre-determined amount.

8. The implantable device of claim 3 wherein the external instrument produces a physical alert when the volume of the urinary bladder reaches a pre-determined amount.

9. A method for determining the volume of a urinary bladder, the method comprising:
    generating one or more light waves from a lighting source located inside of a flexible tube, said lighting source located at one end of said flexible tube, said lighting source electrically connected to electronic circuitry, said flexible tube attached to a surface of a urinary bladder;
    counting a period of time in the electronic circuitry for the light wave to travel from the lighting source to a photocell;
    receiving the one or more light waves at the photocell, the photocell electrically connected to the electronic circuitry;
    calculating a distance that the light wave traveled from the lighting source to the photocell using the period of time;
    comparing the distance in a baseline distance representing a length of the urinary bladder at a known volume; and
    determining the volume of the urinary bladder based on said comparison.

10. The method of claim 9 further comprising alerting a user when the volume of the urinary bladder reaches a predetermined level.

11. The method of claim 9 further comprising reflecting the one of more light waves with reflective material positioned at one end of the flexible tube.

12. The method of claim 9 further comprising the transmission of the period of time, the distance or the volume to an external instrument.

13. The method of claim 12 wherein the transmission uses a Bluetooth protocol.

14. The method of claim 9 further comprising monitoring the volume of the urinary bladder to calculate a rate of increase in the volume of the urinary bladder.

* * * * *